United States Patent [19]

Ekenstam et al.

[11] 4,072,249
[45] Feb. 7, 1978

[54] CONTAINER SUITABLE FOR SMALLER QUANTITIES OF FLUID OR SEMIFLUID SUBSTANCES

[75] Inventors: Bo Thuresson Af Ekenstam, Molndal; Erik Gustaf Percy Nordqvist, Saro, both of Sweden

[73] Assignee: Landstingens Inkopscentral, Solna, Sweden

[21] Appl. No.: 661,177

[22] Filed: Feb. 25, 1976

[30] Foreign Application Priority Data

Mar. 3, 1975 Sweden .............................. 7502318

[51] Int. Cl.² ............................................. B65D 25/38
[52] U.S. Cl. ..................................... 222/95; 222/143; 222/107; 222/210; 222/214; 222/215
[58] Field of Search ................. 222/107, 95, 214, 215, 222/92, 212, 213, 210; 206/820, 484; 128/232

[56] References Cited

U.S. PATENT DOCUMENTS

| | | | |
|---|---|---|---|
| 2,428,577 | 10/1947 | Mathis | 222/214 |
| 2,771,071 | 11/1956 | Mann | 128/232 |
| 2,899,110 | 8/1959 | Parker | 222/215 |
| 3,145,879 | 8/1964 | Williams | 212/212 X |
| 3,154,074 | 10/1964 | Harrison | 222/92 X |
| 3,155,281 | 11/1964 | Stracey | 222/107 |
| 3,295,523 | 1/1967 | Weichselbaum | 222/215 X |
| 3,473,524 | 10/1969 | Drewe | 222/215 X |
| 3,567,463 | 3/1971 | Williams | 206/484 X |
| 3,592,360 | 7/1971 | Alek | 222/107 X |
| 3,626,939 | 12/1971 | Maltenfort | 128/232 |
| 3,851,571 | 12/1974 | Nichols | 206/484 X |

*Primary Examiner*—Allen N. Knowles
*Attorney, Agent, or Firm*—Hane, Roberts, Spiecens & Cohen

[57] ABSTRACT

A container for dispensing fluid and semifluid liquids and pastes, such as for medicinal use, is provided with a top flexible dome and a bottom dome which may or may not be flexible. The contents which are stored in the space between the two domes is squeezed outwardly through a spout on the bottom dome by pressing and forcing the top dome into the bottom dome. The container may be combined with other containers which are connected along flanges of each container, which flanges are used to grip the container by fingers so that when the top dome is pressed downwardly by a thumb the fingers may aid in the process. The plurality of containers connected along the flanges form a block which may be combined with other blocks for easy transport.

11 Claims, 41 Drawing Figures

FIG. 7
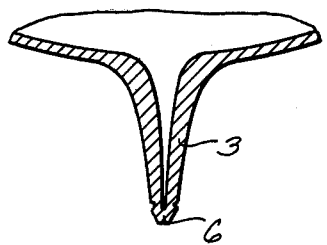
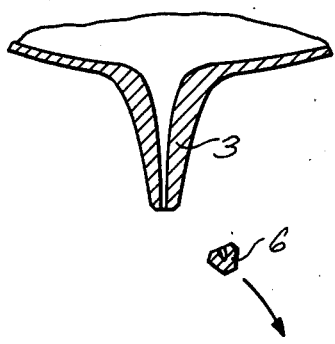
FIG. 8
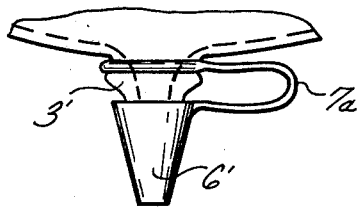
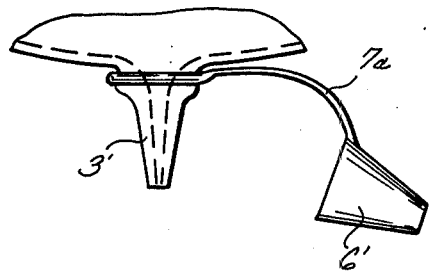
FIG. 9    FIG. 10

FIG. 16
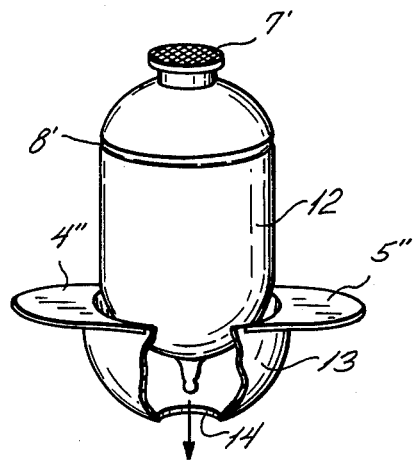
FIG. 17
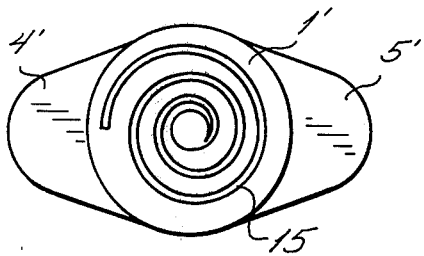
FIG. 18
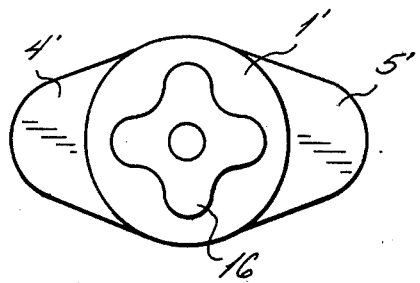
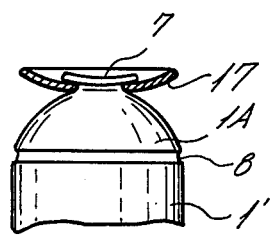
FIG. 19

FIG. 20
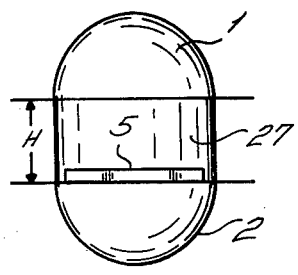
FIG. 22A
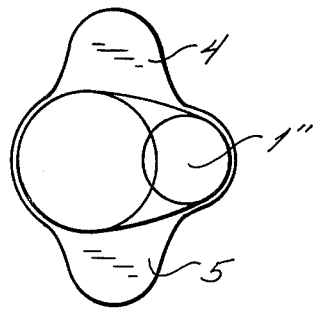
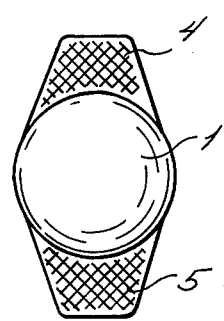
FIG. 20A
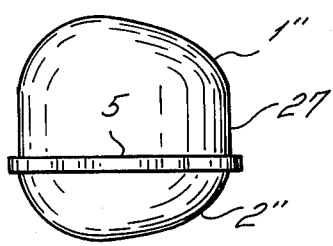
FIG. 22
FIG. 21
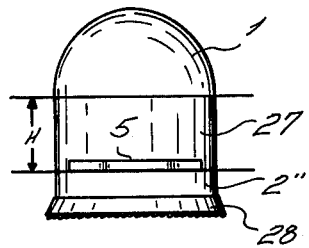
FIG. 23A
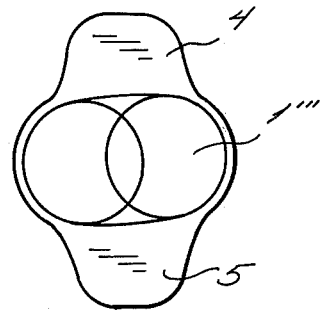
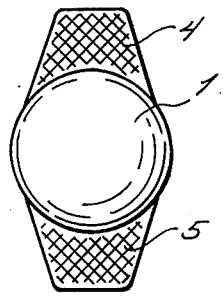
FIG. 21A
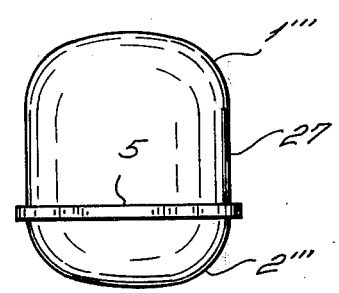
FIG. 23

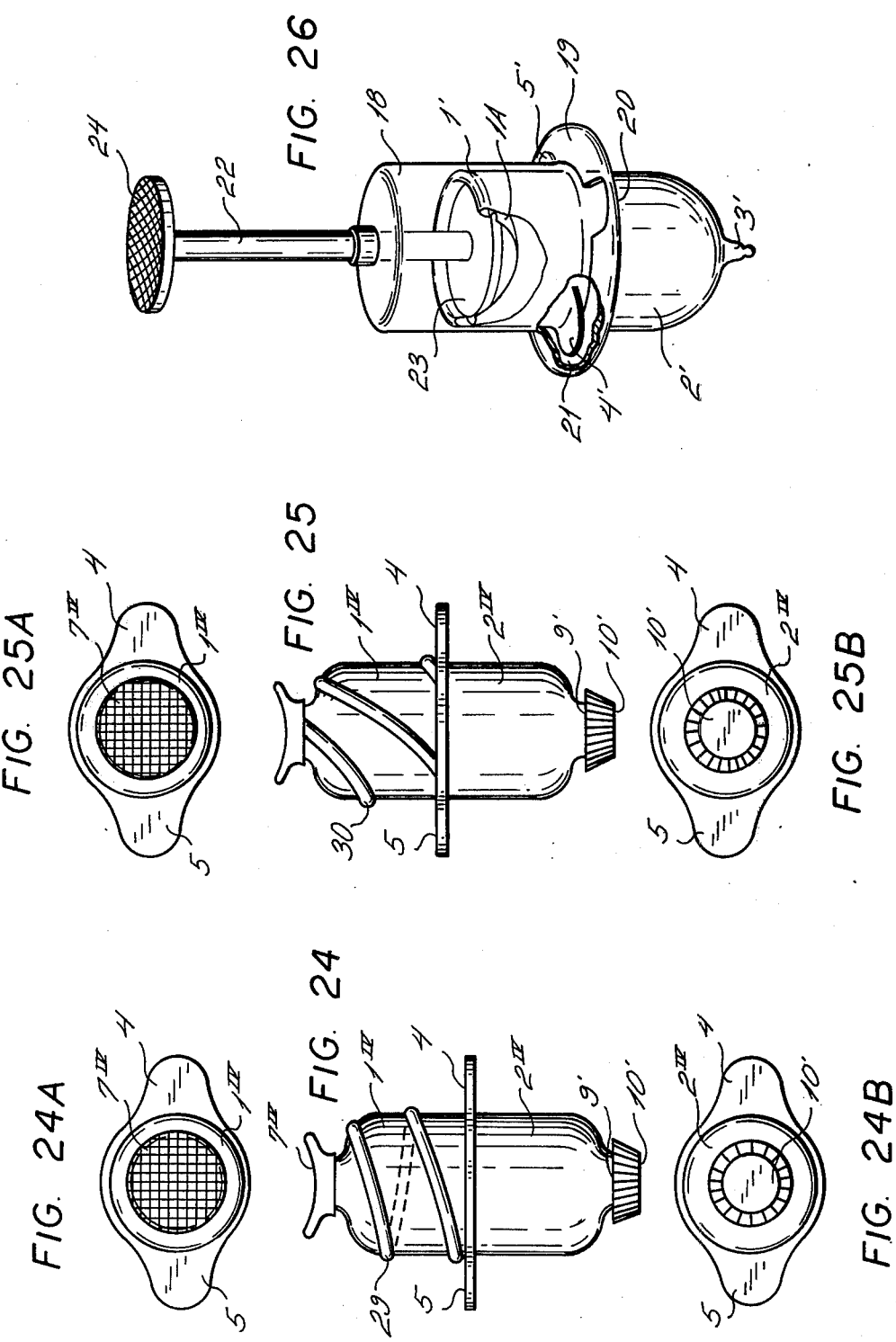

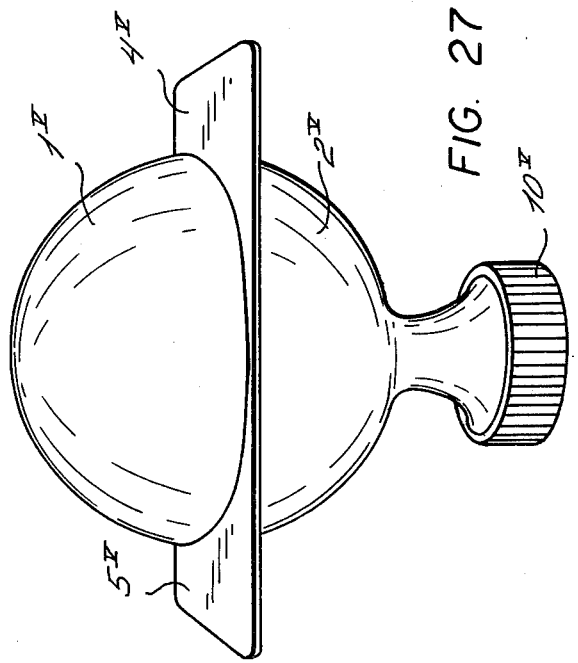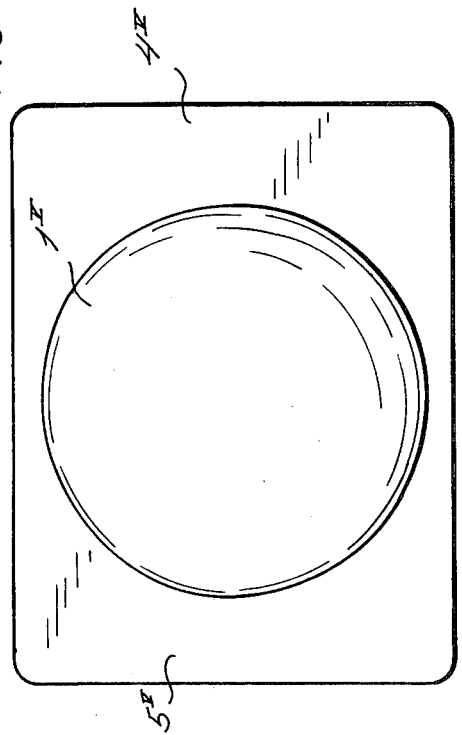
FIG. 27
FIG. 27A
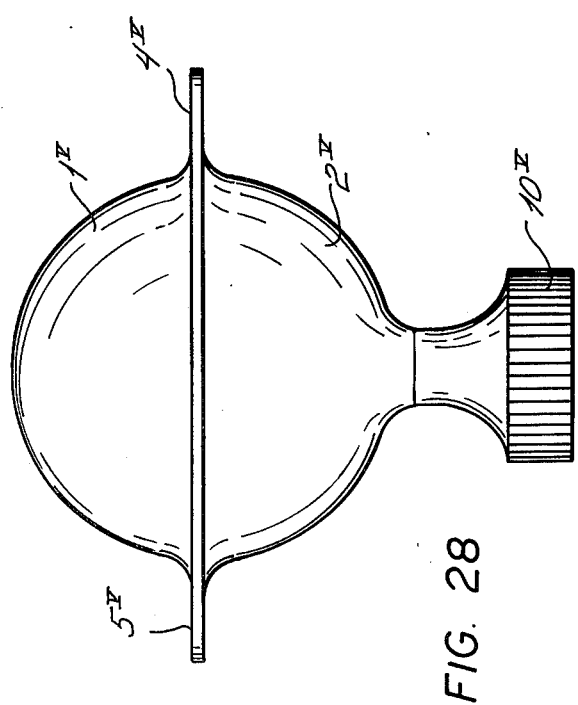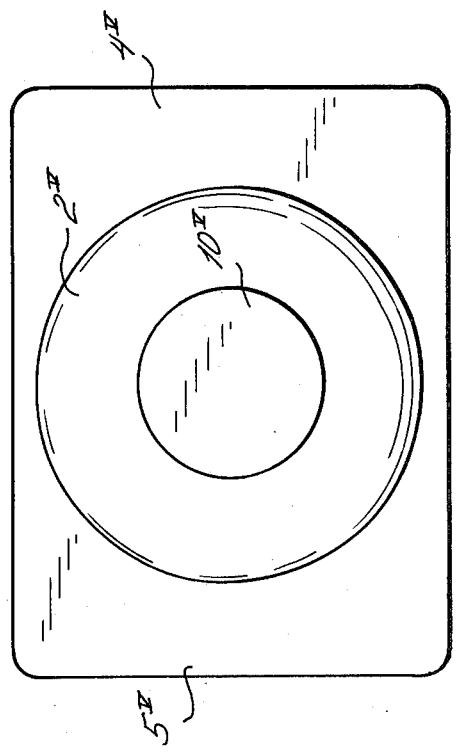
FIG. 28
FIG. 28A

CONTAINER SUITABLE FOR SMALLER QUANTITIES OF FLUID OR SEMIFLUID SUBSTANCES

BACKGROUND OF THE INVENTION

This invention has reference to a container for fluid or semi-fluid substances in small quantities. The substances to be packed according to the invention are mainly drugs consequently the following description deals with such substances. However, it should be obvious that other substances can be packed in the described container. In administering drugs, it is common to pack them in conventional tubes. The medical doctors Mona Hall, Percy Nordqvist, Eva Palmgren and Irene Wilhelmsson have reported in a study at the National Medical Conference 1974 in Sweden, that the conventional tube, irrespective of used material, is very difficult to handle for especially older people. The test tubes used by the doctors have been of various types of existing tubes, containing substances having pharmacological effects. The study is considered to be highly representative for the kind of problems appearing in the use of tubes, and it is related in Svensk Lakartidning 1975 (Swedish Medical Journal).

Tubes are sometimes intended for one-time use and sometimes for repeated use. The tube shall always be such that by squeezing, a predetermined amount of the substance can be applied on a wanted spot of the patient. However experience has shown that it is completely impossible to meet this requirement by using conventional tubes.

In the periodical Nord Emballage, Feb. 1975, Vol. 2, page 4, it is mentioned that it is possible to get more exact doses by using a specially designed valve. This is of course an improvement, but patients have difficulty in handling these tubes equipped with such valves. These kinds of tubes are also expensive, which is a serious disadvantage considering the large consumption of tubes in hospitals.

SUMMARY OF THE INVENTION

The object of this invention is to make a container, which a patient, irrespective of age, can handle without difficulty. According to the invention, the container can be placed between two fingers, and a thumb can be used to squeeze the contents out of the container. The container, according to the invention, has flanges such that it can be gripped by, for example, the index finger and the middle finger. Due to these flanges it is also possible to manufacture blocks of containers, where the containers are joined to each other by the flanges. In the joints between containers, there shall be indications of fracture, facilitating the separation of one container from the block and which can be used by the patient. By having the containers joined to each other they form units which can easily fit into boxes. Packages containing several boxes can have such dimensions that a number of packages can form units of multiple packages. Subsequently, the handling of containers from factory to hospital becomes simpler.

A container according to this invention contains a top-part, a bottom-part, and protruding members forming the flanges that are gripped by the fingers when being squeezed. The bottom-part is normally made of rigid material and the top-part of flexible material. Both the top- and bottom-parts are have a domed shape, preferably spherical or the like. Naturally both parts can be made of flexible material, but when so there must be arranged a rigid envelope having the protruding members thereon and which envelope to a lesser or greater degree, encloses the bottom-part. According to te invention it is appropriate that the top-part is fitted with some kind of a member keeping a thumb securely in place. Such a member can be a friction lining or a particular shape of the upper part.

The top-part might also contain a member, as, for example a spring or other element of metal, arranged such that the position of the top-part remains after having been squeezed.

The container may also have permanent rib shaped deformations or the like such that squeezing the top-part is made against a retaining force.

The top-part of the container might have a circular member arranged such that when the container is squeezed, this circular member scrapes substances sticking to the walls.

The bottom-part of the container might have an opening which can be sealed with a cap. The bottom-part may have any kind of apropriate opening for emptying the container. The opening may be small or big and can be sealed by a cap having a locking device or threads.

The container according to the invention can also be fitted in a special device having a plunger such that the contents can be squeezed out by the plunger. This special device also has members such that it can be gripped by fingers and normally can take the place of the corresponding means of the container.

According to the invention, it is advantageous to make a number of bottom-parts forming one piece and then to fit the top-parts. The separate containers in such a unit can be filled wth substance at the same time, for example via the bottom parts, and when using this method it might be convenient that the top-parts are initially fully depressed into the bottom-parts and that the substance used for filling is preheated.

BRIEF DESCRIPTION OF THE DRAWING

The invention, is described in greater detail in connection with the accompanying drawing wherein, FIG. 7 shows a closed spout of a container, where FIG. 8 shows an open spout, where FIG. 9 shows another embodiment of a closed spout, where FIG. 10 shows the spout of FIG. 9 after being opened, where FIG. 16 shows a perspective view, partly in section, of a container similar to the container of FIG. 12, where both the top part and the bottom part are made of flexible material ad where the bottom part is partly enclosed by an envelope of hard material, where FIGS. 17 and 18 show modifications of the top part of a container and more particularly elements for pressing down the top part toward the bottom part, where FIG. 19 shows a member on the outside of the top part of a container, said member acting as a locking device for holding the top part in position when pressed on by a finger, where FIG. 20 shows an elevational view of a container similar to FIG. 1 but of cylindrical configuration, where FIG. 20A is a top view of FIG. 20, where FIG. 21 shows a cylglobid shape container having a flat bottom, where FIG. 21A is a bottom view of FIG. 21, where FIG. 22 shows a side view of a cylovid shaped container, where FIG. 22A is a top view of FIG. 22, where FIG. 23 shows a side view of a container having a cyleliden shape, where FIG. 23A is a top view of FIG. 23, where FIG. 24 shows a container similar to the one shown in FIG. 11 but with a top part having a spiral-shaped bead acting as a spring, where FIG. 24A is a top view of FIG. 24, where FIG. 24B is a bottom view of FIG. 24, where FIG. 25 shows the same container as in FIG. 24 but with a different spiral bead, where FIG. 25A is a top view of FIG. 24, where FIG. 25B is a bottom view of FIG. 25, where FIG. 26 shows a perspective view of a squeezing device for a container according to one or several of shown embodiments, where FIG. 27 shows a perspective view of the same container as shown in FIG. 1 seen at an angle from the side, the grips for resting the fingers being rectangular so that a number of containers by joints between these grips can form a block, where FIG. 27A is a top view of FIG. 27, where FIG. 28 shows a side view of a container according to FIG. 27, where FIG. 28A is a bottom view of FIG. 27, where

Figure 1:
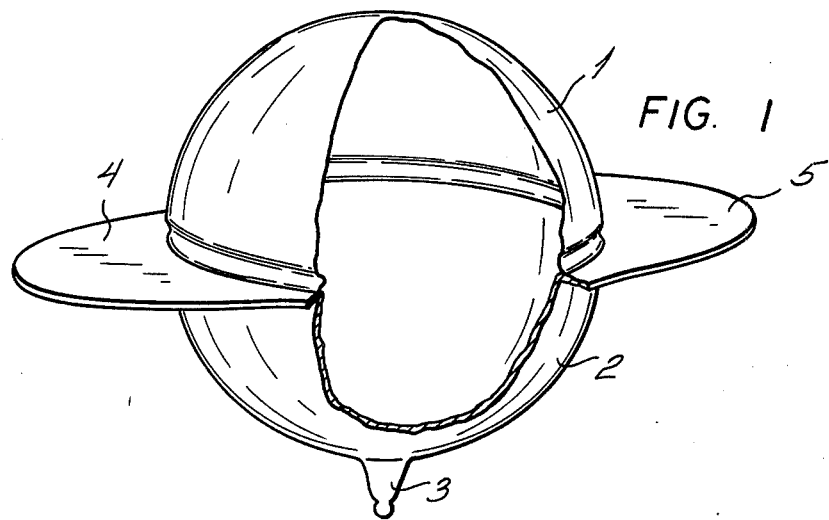
FIG. 1 shows an embodiment of a container according to the invention, either filled or ready to be filled with a substance, where
Figure 3:
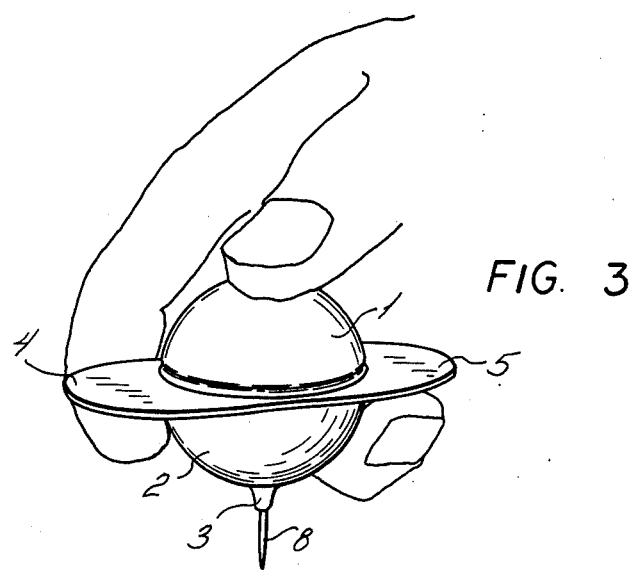
FIG. 3 shows a gripped container in the form of a one-time syringe and just before the squeezing takes place, where
Figure 4:
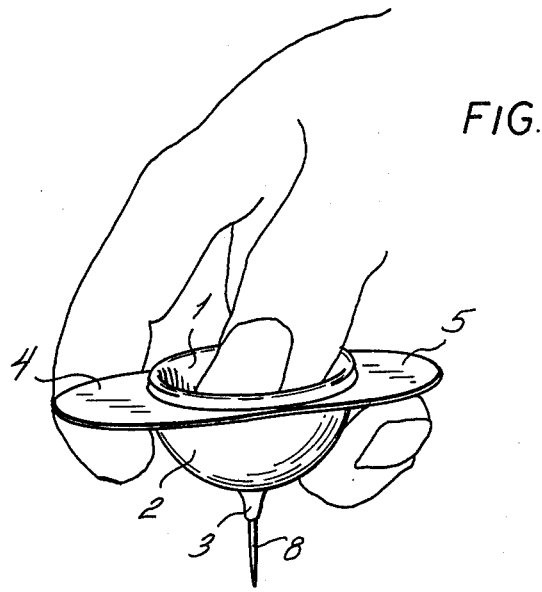
FIG. 4 shows the container of FIG. 3 after it is empited, where
Figure 5:
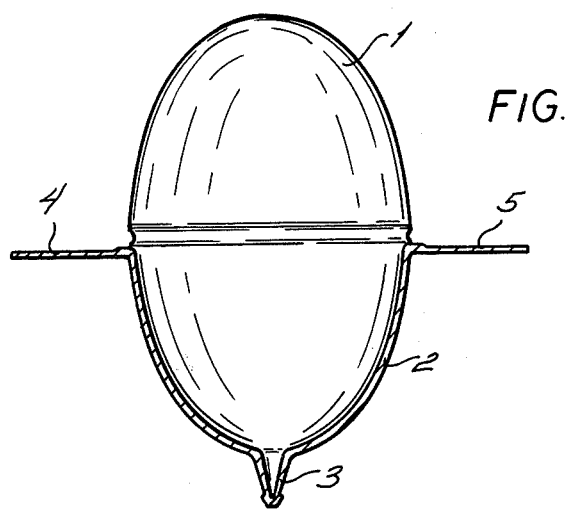
FIG. 5 shows a partial section of the container of FIG. 1, where
Figure 6:
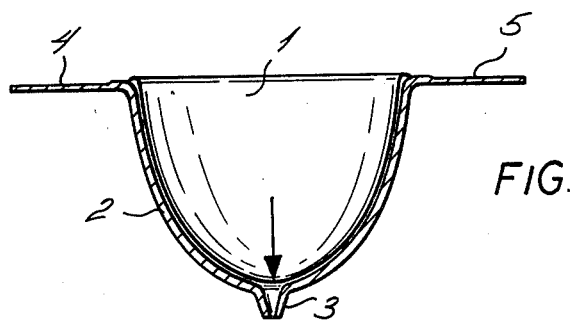
FIG. 6 shows a section of the container shown in FIG. 2, where

In the drawing, reference numeral 1 refers to a dome-shaped part which is made of soft and ductile material. Numeral 2 refers also to a dome-shaped part, which is made of stiffer material and meant to retain its shape. The two dome-shaped parts are with their openings joined to each other as shown in FIG. 1, forming a container which is mainly spherical. However, it is obvious that the two joined parts can have any other shape. They could be for example cubical, rectangular or pyramidal, in other words the shape of the two joined parts can be varied in numerous ways. The two parts can for example be cylindrical and the free ends closed by hemispherical parts. It could be convenient to make a flat top on one of the dome-shaped parts, whereby the container can be placed on a table top or the like without rolling. The dome-shaped part 2 has a sealed spout 3 which can be opened whenever desired. At the joint between the two dome-shaped parts is an encircling lug which is elliptical such that two lips or flanges 4 and 5 are formed. Naturally, the lug can be given any suitable shape. It would be pertinent to keep the size down of the dome-shaped parts in order to facilitate the use of the container as shown in FIGS. 3 and 4. To the spout 3 any suitable means can be connected for applying the substance leaving the spout. Consequently, a hypodermic needle can be connected to the container, when it contains a liquid substance. A flexible or stiff tube could be connected to the container. There are numerous examples of what could be connected to the spout 3.

In the FIGS. 7 and 8 there is shown a spout 3, which has a sealing 6, which together with the spout forms one single unit. This kind of sealing can be cut off as shown in FIG. 8.

FIG. 9 shows a spout 3′, which is sealed by a cap 6′, which is tied by a link 7 a to the spout 3′; or the cap could be tied by the link to the container. FIG. 9 shows the spout 3′ sealed by the cap and FIG. 10 when the cap is off.

Figure 2:
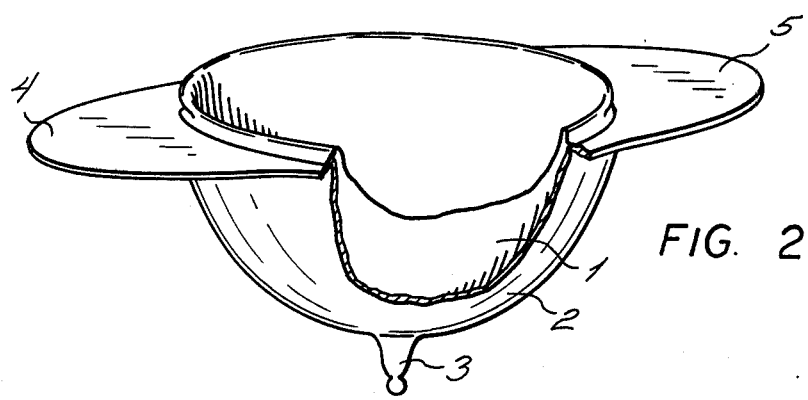
FIG. 2 shows the same container as in FIG. 1 but emptied, where

The container according to the invention shall be such in nature that the dome-shaped part 1 can by squeezing or the like take the shape shown in FIG. 2; in other words the wall of the dome-shaped part 1 is flexible that it, to a lesser or greater extent, adjusts to the inside of the dome-shaped part 2. For the invention subsequently all materials can be used which fullfill the function shown in FIGS. 1 and 2. Suitable material for both parts 1 and 2 would be plastic, where the plastic in part 1 is flexible and in part 2 rather stiff. Naturally, it, be also possible that part 2 is made of metal and part 1 of metal foil. Combinations like stiff and thin cardboard or glass and rubber are also possible.

It would be practicable to construct the wall of part 1 in such a way that when the container has been squeezed the wall remains as it is just before the squeezing finishes. To this end elements like for example ribs of suitable material could be molded as integral parts of part 1. It would also be possible to include additional elements such that the dome-shaped part 1 gets a tendency to instantly switch over to the position shown in FIG. 2, when triggered by pressure on top of part 1.

The container as described is for example used in the following way. The user opens the spout 3; he connects something like, for example, a tube or a hypodermic needle; and then he squeezes the container as shown in FIG. 3. In FIGS. 3 and 4, the container is fitted with a hypodermic needle 8. Holding the container as shown in FIG. 3, the needle is inserted in the part of the body to receive the injection. Now the user uses his thumb to press the top of the dome-shaped part 1 as shown in FIG. 4, the pressure is being applied until part 1 is in the position shown in FIGS. 2 and 4, whereby the container is emptied.

Figure 11:
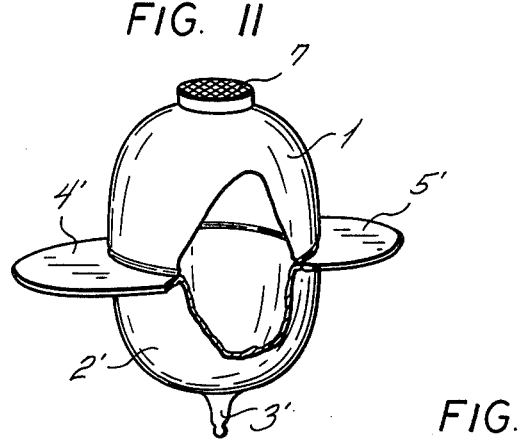
FIG. 11 shows a perspective view of a container similar to the container in FIG. 1, however having a more cylindrical shape and fitted with a grip for a squeezing finger, where

FIG. 11 shows a container similar to the above described and where both dome-shaped parts are indicated respectively with 1′ and 2′. They differ from the dome-shaped parts above in that they are cylindrical and one end of each part forms a hemisphere. The dome-shaped part 1' has on its top a protuberance 7 suitably shaped to be pressed by a finger. The protuberance can of course have a smooth surface, but it would be more adequate that the surface has such properties that a finger does not slip when pressing the container.

Figure 12:
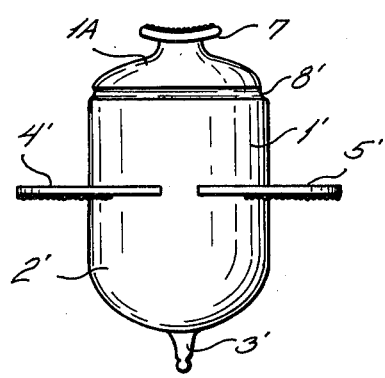
FIG. 12 shows partly in section a container similar to the container in FIG. 11 but modified such that it has a dished circular bead, designed to act as a member for scraping substances as may be sticking to the walls when emptying the container, where
Figure 13:
FIGS. 13 and 14 show details of the container of FIG. 12 in two different operational stages, where
Figure 12A:
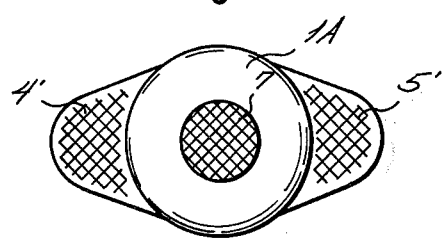
FIG. 12A is a top view of FIG. 12, where
Figure 14:
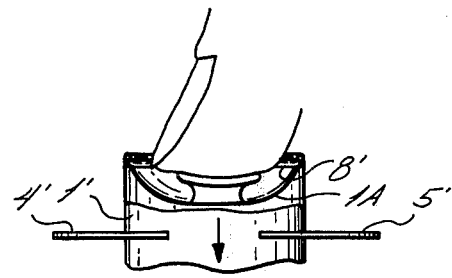

The container in FIG. 12 differs from the one in FIG. 11 in that the dome-shaped part 1' has a recessed circular bead 8', preferably situated where the cylindrical shape turns into hemispherical shape. The hemispherical part of the dome-shaped part 1' is indicated with the number 1A. The circular bead 8' is designed to act as a member scraping the substance sticking to the walls when emptying the container. This is especially shown in FIG. 14, when part 1A is pressed down. It shows how the circular bead 8' fits into the cylindrical part of the container.

FIG. 16 shows a container made in one piece which is indicated with the number 12. The shape of the container is like the container according to FIG. 11. The container 12 is made of flexible material and in order to have necessary rigidity the end with the spout has an envelope 13 of hard material. The envelope has two flanges 4" and 5" for the fingers, similar to the flanges 4' and 5'. The envelope also has an opening 14 for the spout. The container has a circular bead as described in connection with FIG. 11 and also a protuberance 7'.

FIG. 17 shows how the top-part 1' can have an integrally moulded spiral 15, the objective of which is to distribute applied pressure to a greater area of the top of part 1' when emptying the container.

FIG. 18 shows another integrally moulded element 16 having the same function as the spiral in FIG. 17.

The two elements in FIGS. 17 and 18 can be made of any material as long as they function as desired.

FIG. 19 shows the top-part of a container according to FIG. 12 fitted with a disc 17 shaped somewhat like a plate and with its outer edge pointing out from the container. In the center, the disc has a hole matching and fixed to the protuberance 7 on the part 1A. The disc can be made of any suitable material, for example plastic or metal and it may be resilient. The purpose of the disc 17 is to act as a catching device inside the cylinder being formed when part 1' is pushed. When pressure on the protuberance 7 ceases, the disc 17 prevents the part 1' from springing back. How the cylinder is formed is, for example, shown in FIG. 14.

The containers according to FIG. 1 or to FIG. 11 naturally can be used in a device containing a plunger replacing a human thumb. Some important embodiments will be described.

FIG. 20 shows a container having a central part 27 of a length H which central part preferably has a noncircular cross section. However, a container can be made having a cylindrical central part with hemispheres as top-part 1 and bottom-part 2. This embodiment, having the length H greater than zero, is given the names cylglobid and embodiment 1. If the length H is equal to zero, the container becomes the same as shown in FIG. 1.

FIG. 21 shows the same container as in FIG. 20 but where the bottom-part 2" has a large opening covered by a lid 28.

The embodiments according to the FIGS. 22 and 23 are given shapes which are optional with regard to adapting to fingers, when using the thumb together with the index finger and the middle finger for emptying the container.

In FIG. 22, the top-part 1" is adopted to the shape of the thumb. The fingerprint of the thumb in combination with the cross-section of the tip of the thumb forms volume alike half an egg cut from tip to tip. When the container is made with a central part 27 and a top-part and a bottom-part shaped like the said volume, it will be easy using the thumb, the index and the middle fingers to press the top-part 1" through the central part 27 down to the corresponding bottom-part 2". The spout is preferably positioned in the lowest area of the bottom-part. If the container is made without a central part, which is the same as $H = 0$, it takes the shape of an egg. The embodiment having the length H greater then zero, as shown in the figure, is known as the cylovid.

FIG. 23 shows a contaner having a top-part 1'" and a bottom-part 2'", each part being shaped like a semi-ellipsoid when the cutting is made along the biggest diameter. When such top- and bottom-parts are joined with a central part 27, an embodiment is formed called the cylelid. If the length H of the central part is equal to zero, the shape of the container will be a full ellipsoid.

Common for all the embodiments according to the FIGS. 20 – 23 is that when H is greater than zero, the top- and bottom-parts are separated by an envelope surface forming the central part, which envelope surface is theoretically formed when a generatrix is moved perpendicular to and along all of the envelope of the maximum cross section of an end part.

FIG. 24 shows a container corresponding to the one shown in FIG. 11. On the top-part $1^{IV}$ is arranged a spiral-shaped bead 29. The container has, like the ones previously described, a part $7^{IV}$ for a thumb and two flanges 4 and 5, for gripping by the forefinger and the middle finger when used, and additionally a bottom-part $2^{IV}$. The bottom-part has an opening 9' which can be sealed with a cap 10'. The spiral-shaped bead 29 gives a resistance to the pressure from a thumb, facilitating conditions for a smooth and controlled application of the substance stored in the container.

FIG. 25 shows a container having exactly the same properties as the container in FIG. 24, but where the single bead is modified such that the top-part has a number of beads as shown by the diagram.

FIG. 26 shows a device for emptying a container according to the invention.

The device has a cylindrical cap 18, which at its open end has a circular pocket 21 formed by a doublefolded corbelled rim 19 and 20. The circular pocket 21 is intended to surround the flanges 4' and 5' for the fingers of a container 1', 2'. The cap 18 is fitted with a plunger 22 which has a press plate 23 and a finger part 24. For emptying a container according to this invention using a device as described, all the unit is placed between two fingers in such a way that part 20 of the rim is gripped by said fingers. The thumb is put on the fingerpart 24, and by pressing the plunger 22 the container 1', 2' is emptied.

Figure 15:
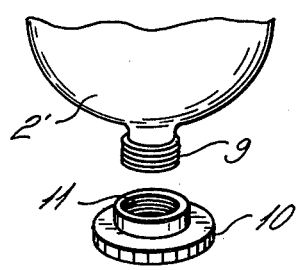
FIG. 15 shows an exploded view of the bottom part of a container having an opening with a screw cap, where

The spout 3 can be made cylindrical and with threads 9 as shown in FIG. 15. A cap 10 is adapted to the spout by corresponding threads 11.

Again, it should be noted that all the flanges of the container adapted to the fingers are done such that the emptying is made smoothly and controllably. This implies that the design work has to be based on an empirical study of the fingers and their physiological coordination. Embodiments and sizes of said containers should be designed taking a number of parameters into consideration, like for example length, angle, surface and volume of fingertips, fingerjoints and all the fingers in order to have optimal effects and as few types as possible.

Figure 29:
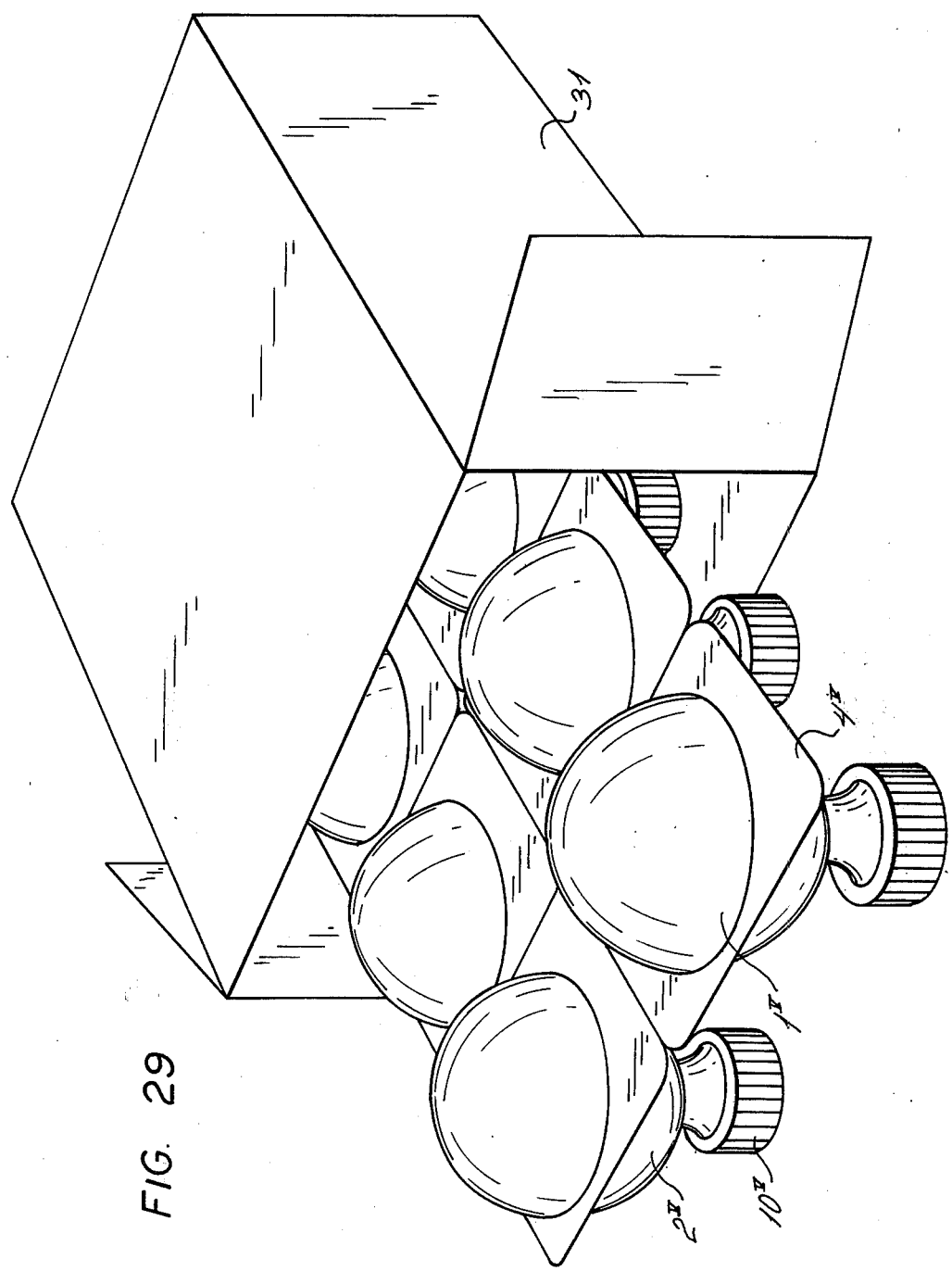
FIG. 29 shows a number of containers forming a block which can be slid into a box, and where
Figure 30:
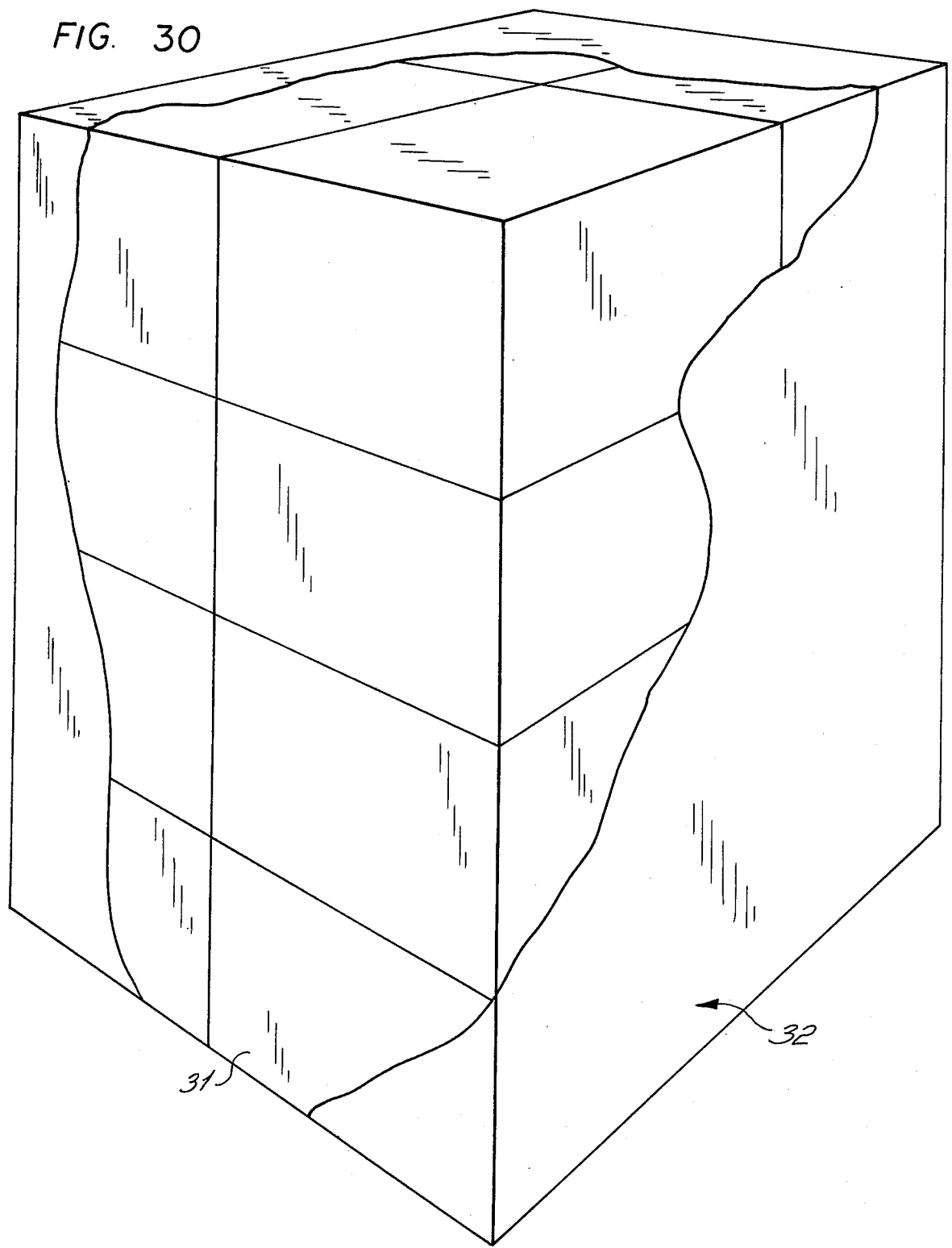
FIG. 30 shows a unit containing a number of the boxes shown in FIG. 29.

FIGS. 27 and 28 show a container having a top part $1^V$ and a bottom-part $2^V$. The container has two flanges $4^V$ ad $5^V$ together forming a rectangular surface. The bottom-part $2^V$ has an opening with a sealing organ $10^V$ which is cylindrical and prevents the container from staying upright on a horizontal surface. Because of the rectangular shape of the flanges a number of containers can be joined to each other, forming a block as shown in FIG. 29. Between the flanges are indications of fracture making it possible to break off one container at a time from the block. By making blocks of containers, these blocks can conveniently be packed in boxes 31 which boxes can form multiple, packages enclosed in wrapping 32, such as, for example, thermoplastic foil.

When manufacturing the blocks according to FIG. 29, the bottom-parts together with the flanges can be made in one step in one tool, after which this part is fitted with the top-parts, separately made or equally made as one unit.

We claim:

1. A container for dispensing fluid and semi-fluid liquids or pastes, comprising: a top dome having a first closed end and a second open end and made of a flexible material so that said first closed end may be pressed downwardly toward and through said second open end; a bottom dome also made of a flexible material and having a first closed end and a second open end, said second open ends of each of said domes being connected to each other so that when said top dome is pressed downwardly said first closed end of said top dome passes through said second open end of said top dome and said second open end of said bottom dome toward said first closed end of said bottom dome; means located on said bottom dome near said first closed end thereof for allowing the contents in said top and bottom domes to exit therefrom to a desired point outside of said container; flange means surrounding said top and bottom domes near said connected second open ends for gripping by fingers so that the contents of the container may be forced outwardly through said means for allowing when a thumb presses downwardly upon said first closed end of said top dome to thereby force said top dome into said bottom dome while at the same time forcing the contents out through said means; and an envelope surrounding said bottom dome and made of a rigid material to thereby support said bottom dome when said top dome is pressed and forced thereinto, said flange means being mounted about said envelope.

2. A container for dispensing fluid and semi-fluid liquids or pastes, comprising: a top dome having a first closed end and a second open end and made of a flexible material so that said first closed end may be pressed downwardly toward and through said second open end; a bottom dome having a first closed end and a second open end, said second open ends of each of said domes being connected to each other so that when said top dome is pressed downwardly said first closed end of said top dome passes through said second open end of said top dome and said second open end of said bottom dome toward said first closed end of said bottom dome; means located on said bottom dome near said first closed end thereof for allowing the contents in said top and bottom domes to exit therefrom to a desired point outside of said container; flange means surrounding said top and bottom domes near said connected second open ends for gripping by fingers so that the contents of the container may be forced outwardly through said means for allowing when a thumb presses downwardly upon said first closed end of said top dome to thereby force said top dome into said bottom dome while at the same time forcing the contents out through said means; and said top dome further comprising thumb gripping means positioned at said first closed end, whereby a thumb pressing down on said second closed end of said top dome does not slip therefrom; means surrounding said thumb; gripping means for holding said top dome in said bottom dome after said top dome has been pressed and forced into said bottom dome to squeeze out the contents of the container, said means for holding having a central opening for receiving therethrough said thumb gripping means and an upwardly extending outer edge pointing away from said second open ends.

3. A container for dispensing fluid and semi-fluid liquids or pastes, comprising: a top dome having a first closed end and a second open end and made of a flexible material so that said first closed end may be pressed downwardly toward and through said second open end; a bottom dome having a first closed end and a second open end, said second open ends of each of said domes being connected to each other so that when said top dome is pressed downwardly said first closed end of said top dome passes through said second open end of said top dome and said second open end of said bottom dome toward said first closed end of said bottom dome; means located on said bottom dome near said first closed end thereof for allowing the contents in said top and bottom domes to exit therefrom to a desired point outside of said container; flange means surrounding said top and bottom domes near said connected second open ends for gripping by fingers so that the contents of the container may be forced outwardly through said means for allowing when a thumb presses downwardly upon said first closed end of said top dome to thereby force said top dome into said bottom dome while at the same time forcing the contents out through said means; and mechanical dispensing means for said top dome, said mechanical dispensing means comprising a plunger having a press plate for reciprocable movement to force said top dome into said bottom dome, and a double rim consistuting a pocket for the reception therein of said flange means so that said mechanical dispensing means can be supported on said top dome and so that said rim may be gripped by fingers to force the contents out through said bottom dome by said plunger.

4. A plurality of containers connected together to form a block of containers which may be easily transported and shipped, each of said plurality of containers comprising: a top dome having a first closed end and a second open end and made of a flexible material so that said first closed end may be pressed downwardly toward and through said second open end; a bottom dome having a first closed end and a second open end, said second open ends of each of said domes being connected to each other so that when said top dome is pressed downwardly said first closed end of said top dome passes through said second open end of said top dome and said second open end of said bottom dome toward said first closed end of said bottom dome; means located on said bottom dome near said first closed end thereof for allowing the contents in said top and bottom domes to exit therefrom to a desired point outside of said container; and flange means surrounding said top and bottom domes near said connected second open ends for gripping by fingers so that the contents of the container may be forced outwardly through said means for allowing when a thumb presses downwardly upon said first closed end of said top dome to thereby force said top dome into said bottom dome while at the same time forcing the contents out through said means; said flange means being of rectangular shape and surrounding said top and bottom ends, said containers being connected together at said flange means.

5. The container according to claim 4, wherein said bottom dome is made of a rigid material that is nonyielding.

6. The container according to claim 4, wherein said means for allowing comprises a spout positioned at said first closed end of said bottom dome, and means for selectively closing off or opening up said spout to permit the contents of said container to exit.

7. The container according to claim 6, wherein said means for selectively closing off and opening up said spout comprises a cap, and linking means connecting said cap to said spout so that said cap may pivot thereabout, whereby when said cap is mounted over said spout said spout said spout is closed off, and when said cap is pivoted away from said spout said spout is opened up.

8. The container according to claim 6, wherein said means for selectively closing off and opening up said spout comprises a threaded cap, and said spout comprises mating threads thereon for said threaded cap, whereby said threaded cap may be rotated in a first direction to close off said spout and a second direction to remove said threaded cap and open up said spout.

9. The container according to claim 4, wherein said top and bottom domes are both shaped as a hemisphere so as to form a container shaped as a sphere.

10. The container according to claim 4, further comprising means for connecting said second open ends of said top and bottom domes, and said flange means being mounted about said means for connecting, whereby said container takes on a shape that is elongated.

11. The container according to claim 4, wherein each of said top and bottom domes is shaped as a cylinder and said first closed ends of each of said top and bottom domes has a hemispherical shape.

* * * * *